United States Patent
Huber et al.

(10) Patent No.: US 9,215,963 B2
(45) Date of Patent: Dec. 22, 2015

(54) MEDICAL INSTRUMENT CONTAINING AN ADHESIVE SEAL WITH FILLER

(75) Inventors: Matthias Huber, Emmingen-Liptingen (DE); Peter Eisenkolb, Tuttlingen (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 621 days.

(21) Appl. No.: 12/428,953

(22) Filed: Apr. 23, 2009

(65) Prior Publication Data
US 2009/0258174 A1  Oct. 15, 2009

Related U.S. Application Data

(63) Continuation of application No. PCT/EP2007/009135, filed on Oct. 22, 2007.

(51) Int. Cl.
*B32B 1/02* (2006.01)
*A61B 1/00* (2006.01)
*A61B 1/307* (2006.01)
*B32B 1/08* (2006.01)

(52) U.S. Cl.
CPC ............ *A61B 1/00066* (2013.01); *A61B 1/307* (2013.01); *Y10T 156/10* (2015.01); *Y10T 428/1372* (2015.01)

(58) Field of Classification Search
CPC ............ Y10T 428/1372; Y10T 156/10; A61B 1/00066; A61B 1/307
USPC ............ 428/34.1, 34.2, 35.7, 35.9, 36.9
See application file for complete search history.

(56) References Cited

U.S. PATENT DOCUMENTS

| | | | | |
|---|---|---|---|---|
| 4,808,639 A | * | 2/1989 | Chernack | 523/211 |
| 5,059,209 A | * | 10/1991 | Jones | 623/18.11 |
| 6,284,817 B1 | * | 9/2001 | Cross et al. | 523/220 |
| 6,328,691 B1 | * | 12/2001 | Rudischhauser | 600/176 |
| 6,642,344 B1 | * | 11/2003 | House et al. | 528/91 |
| 2005/0288554 A1 | | 12/2005 | Miyagi et al. | |

FOREIGN PATENT DOCUMENTS

| | | |
|---|---|---|
| DE | 69923388 T2 | 12/2005 |
| EP | 0978251 B1 | 1/2005 |
| EP | 1847213 A1 | 10/2007 |
| GB | 1122672 | 8/1968 |

(Continued)

OTHER PUBLICATIONS

International Search Report; PCT/EP2007/009135; Jan. 30, 2008; 3 pages.

(Continued)

*Primary Examiner* — Marc Patterson
(74) *Attorney, Agent, or Firm* — Whitmyer Group LLC

(57) ABSTRACT

A method for filling a hollow space in an autoclavable medical instrument with an adhesive containing a filler has the steps of providing an adhesive with a low viscosity allowing the adhesive to enter into a hollow space in a medical instrument, providing a filler of solid particles within said low viscosity adhesive, density of said solid particles differ from a density of said low viscosity adhesive, filling that hollow space in said medical instrument with that low viscosity adhesive containing said solid particles, allowing said particles a period of time for crowding together into a minimum of space, and curing said adhesive after said period of time.

8 Claims, 3 Drawing Sheets

(56) References Cited

FOREIGN PATENT DOCUMENTS

| | | | |
|---|---|---|---|
| JP | 59214006 | A | 12/1984 |
| JP | 03081717 | A | 4/1991 |
| JP | 08071031 | A | 3/1996 |
| JP | 2002238834 | | 2/2002 |
| JP | 2003126023 | | 5/2003 |

OTHER PUBLICATIONS

German Search Report; Application No. 10 2006 050 969.2; Apr. 18, 2007; 2 pages.
International Preliminary Report on Patentability & Written Opinion of the International Searching Authority; PCT/EP2007/009135; May 5, 2009; 9 pages.

* cited by examiner

MEDICAL INSTRUMENT CONTAINING AN ADHESIVE SEAL WITH FILLER

CROSS-REFERENCE TO RELATED APPLICATIONS

The present application is a continuation of pending International patent application PCT/EP2007/009135 filed on Oct. 22, 2007 which designates the United States and claims priority from German patent application 10 2006 050 969.2 filed on Oct. 23, 2006.

BACKGROUND OF THE INVENTION

The invention concerns a medical instrument and in particular a method for filling a hollow space in an autoclavable medical instrument with an adhesive containing a filler.

In the production of medical appliances, it is customary, when assembling the instrument, for certain structural parts to be connected to one another or imbedded using an adhesive seal. The first purpose of the adhesive seal is to position and fix the structural parts relative to one another, which is achieved by the cured adhesive. Another important point is to ensure a sealed connection between these structural parts, in order to avoid contaminants from the outside being able to penetrate into the interior of the instrument. Such contaminants can include body fluids or tissue fluids with which the medical instrument comes into contact during surgical use. However, contaminants can also include gaseous or liquid cleaning agents that are used in the cleaning and sterilizing procedures carried out after the medical interventions. These can be very aggressive cleaning agents, for example cleaning agents containing peroxide. Moreover, during autoclaving, in particular during what is called flash autoclaving, the instruments are heated to temperatures in access of 145° C. and are very rapidly cooled down again. In practical application, it has now be found that these extreme loads which act repeatedly on a surgical instrument, for example a frequently used endoscope, gradually leads to cracks in the adhesive seal.

This results not only from the extreme thermal loads or stresses that arise during the autoclaving itself. Instead, the formation of cracks is also promoted by the fact that the adhesive, which is composed of a cured plastic material, mostly fills space between metal materials, in most cases medical-grade steel. These metallic materials have different thermal properties than the adhesive as such. Not only can cracks develop in the adhesive itselves for this reason, but the adhesive also partially detaches itself from the contact face with the mostly metal material that is cast with the adhesive.

In long-term applications, therefore, contaminants can gradually penetrate from the outside through these cracks into the interior of the medical instrument. These contaminants compromise the operating safety of the instrument.

From British patent specification 1,122,672 a medical instrument which is a mouth mirror is known. A distal mounting plate serves for mounting a mirror via an adhesive to the mounting plate. The adhesive is mixed with a metal powder, for example iron powder or aluminum powder. Due to this the thermal conductivity of the adhesive is enhanced remarkably. With that method thermal stresses can be reduced with the result, that there is no risk that the mirror releases from the mounting plate after several sterilization processes.

It is an object of the present invention to provide a method for filling a hollow space in an autoclavable medical instrument with an adhesive containing a filler allowing the filler particles to come very close together in the resulting composite.

It is further an object of the present invention to provide an autoclavable medical instrument having a hollow space therein said hollow space being filled with a composite containing a cured adhesive having distributed solid particles therein.

SUMMARY OF THE INVENTION

The object is achieved by a method of filling a hollow space in an autoclavable medical instrument with an adhesive containing a filler, which method comprises the steps of providing an adhesive with a low viscosity allowing the adhesive to enter into a hollow space in a medical instrument, providing a filler of solid particles within that low viscosity adhesive, a density of said solid particles differs from a density of said low viscosity adhesive, filling said hollow space in said medical instrument with said low viscosity adhesive containing said particles, allowing said particles a period of time for packing together into a minimum of space, and curing said adhesive after said period of time.

By using the adhesive as a low viscosity liquid, it can penetrate in small hollow spaces or narrow gaps which have to be filled without the risk that air bubbles or other inclusions were enclosed. Due to the fact that the particles have a density which differs from the density of the low viscosity adhesive either a suspension occurs or the particles are swimming on the low viscosity liquid. Due to the time period provided the particles can pack together into a minimum of space.

If one takes the example, that the particles have a density higher than the density of the low viscosity adhesive, the particles tend to sink down in the direction of gravity. During filling in the mixture of low viscosity adhesive and the particles these are distributed more or less statistically within the liquid and are swirled due to the filling process. After filling in the particles sink down and pack together into a minimum of space. This means they pack itself to the closest arrangement which allows the respective geometry of the particles. This packing or crowding can be enhanced by knocking against the medical instrument or by vibrating it.

If one takes the example of spherical particles, i.e. balls, it is possible to crowd or pack the particles very close to the theoretical sphere packing. This closest spherical packing will fill a space by 74%. Only the spaces between the individual particles and the spaces between the particles and the walls of the hollow space are filled with the low viscosity adhesive. It is possible to fill the hollow space step by step in such a manner. First one inserts or passes the low viscosity adhesive together with the filler particles within to the hollow space and allow the particles to sink downwards the direction of gravity and crowd or pack them together. With that, it is possible to fill relative large hollow spaces step by step with the particles. A surplus of liquid adhesive is removed or put away. If it is not necessary to fill the entire hollow space with particles, it is also possible to fill only particular areas in this space, where high thermal stresses occur. That areas may be small or narrow gaps between two parts welded one to another. With that, one can avoid that extreme thermal stresses crack the adhesive and contaminants can penetrate from the outside. After having filled and crowded or packed the particles, the adhesive is cured.

The resulting composite is a material which volume is occupied in a high extent by the body of the particles. By choosing the material of the particles composites can be signed having desired properties in particular to withstand the thermal and mechanical stresses for a long time. The particles can give the composite electrically conductive or electrically isolating properties depending what kind of material is chosen. The expert has a lot of materials in hand which allows him to design a composite material depending on the materials surrounding the hollow space into which the adhesive/filler mixture have to be filled in. One can perform optimum heat bridges which remarkably reduce inner stresses within the composite material.

In the medical area, most constructional parts are made from metal, in particular of medical-grade steel. If one selects the particles to be added into the adhesive from powders of respective medical-grade steel one can achieve very low thermal stresses between the particles embedded in the cured adhesive and the walls of the hollow space containing it. It is possible to design a composite having a high volume grade of the particle. The result is a composite material which is close to a metallic sinter material than to an adhesive. This composite shows a high thermal conductivity and therefore the building of thermal stresses can be avoided nearly totally.

As mentioned above, it is also possible to use particles having a smaller density than the liquid adhesive, for example by using fillers made of glass or plastic materials. These particles then will swim on the surface of the adhesive.

In that case the crowding or packaging of the particles is not performed by continuously sinking of additional parts. It is done vice versa, by having swimming more and more of such materials. In that case one does not fill the hollow space by packing from downwards to upwards, but opposite, by packing from upwards to downwards.

This method allows the expert to react on different materials which have to be put together with the adhesive.

In a further development of the invention the material of the particles is chosen in that that material has thermal properties close to the thermal property of the constructional element of said medical instrument.

As mentioned above, this results in a composite material having properties which are very very close to the thermal properties of the walls surrounding the hollow space having the composite therein. Additionally, it is possible to use materials which, beside the thermal properties also have mechanical or electrical properties which are close to the materials of the walls surrounding the hollow space or the material the medical instrument is made of.

It is also possible to introduce particles with different densities into the low viscosity adhesive, i.e. particles which sink down and particles which swim on the surface resulting in a composite which have different properties on the lower and the upper side. This can be used for example if one wants to fill a hollow space between two shafts which are inserted one into another and where one shaft is made of medical-grade steel and the other shaft of a plastic.

The instrument is hold in an orientation, that the parts with properties close to the plastic, for example swim on the upper side and the parts with properties close to steel sink down to the bottom. The resulting cured body in the hollow space has on one side properties which are very close to the properties of the material of the shaft made of plastic and on the other side properties which are very close to the material the metallic shaft is made. Additionally, he can take attention to particles having the necessary mechanical stability of maybe damping properties to reduce mechanical or thermal stresses.

In a further embodiment of the invention the size and the shape of the particles are chosen in that the spaces between the particles are such small spaces, that the cured adhesive can withstand thermal stresses acting on that cured adhesive.

This measure is based on following considerations. Low viscosity adhesives usually cure to relatively brittle, hard, glass-like materials. But they nevertheless have up to a certain thickness thermal properties which can also withstand the thermal stresses during an autoclaving process. Gaps or braking out of materials can be recognized starting form relative compact and thick layers. From the producers of such adhesive data of the minimum layer which can withstand thermal sources are published.

With that information in hand one can choose the shape and the size of the particles in that the resulting spaces between the packed or crowded particles are so small that the cured adhesive material as such can withstand the thermal stresses in the area between the neighboring particles.

If one again takes the example of spherical particles it is possible to calculate the maximal distance within the closest ball package between the balls of a certain size. If this maximal distance is in accordance with the above-mentioned specification of the manufacture of the adhesive the adhesive itself can withstand the thermal stresses during autoclaving processes. Nevertheless, the amount of cured adhesive needs to be sufficient to build up a strong composite.

This is also valid for particles having other shapes than balls.

If one does not want to fill the spaces between the particles with adhesive only, it is possible to design a mixture of particles, i.e. relative large and relative small particles, the shape and size of the small particles is chosen in that, it can fit into the free spaces between the packed large particles.

In a further embodiment of the invention, the particles have a size in a range of 50 μm to 150 μm.

It was recognized that this range of particle size is very useful in medical instruments since these small particles can be used to close or fill the small hollow spaces, gaps or niches present in a medical instrument.

In a further embodiment of the invention the particles of the filler are made of metallic material, glass balls, carbide, plastic or ceramic parts. It can be used electrical conductive and/or thermally conductive or electrical isolating and/or thermal isolating materials for achieving the desired properties.

The particles can be spherical, disc-like, ring-like, cubic and polyhedral particles.

The election of materials and geometrical shape allows the expert to design different composites which are of optimum for the particular case.

In a further embodiment of the invention the amount per volume of the particles, prior to curing the adhesive, is in the range of 20 to 80%.

It was recognized, that in that volume range the adhesive of low viscosity together with the particles therein can be handled very good. During use and during cleaning and sterilization medical instruments of this kind show very good properties.

In a further embodiment of the invention the method is performed in that within the final cured adhesive, the volume percentage of the particles is 50 to 80%.

This method has the advantage, that the resulting composite material shows properties which are determined by the properties of the filler material rather than by the properties of the cured adhesive. The cured adhesive has merely the task to hold the different parts of the composites together and to hold the composite within the hollow space where it is build up.

Therefore, two requirements are to be fulfilled by the composite, first an intensive and sealing adhesion of the parts and second to perform a close and sealing composite for a long time.

The fact, that the resulting composite can withstand the extreme thermal changes during autoclaving in the medical field, opens the possibility to mold in preformed parts into the composite.

For example, for complicate channels which cannot be performed by machining, it is possible to perform such channel directly within the composite. For it, it is possible to first position within complicated formed hollow spaces, wires or cords, following by molding the adhesive together with a filler into that hollow space. After curing of the adhesive the cord or wire can either be withdrawn to perform channels or, they can stay within the composite for other purposes. If a cord is made from a low melting material it is possible to remove the cord by melting, burning or the like.

It is also possible to first insert into the hollow space, fiber-like or channel-like additional filler pieces followed by performing the method for filling the hollow space. The resulting hollow channels show honeycomb structures with strong mechanical properties can result.

This can be done, since it is possible to use the method with relative large spaces also, since only minor amounts of adhesive will remain in the spaces between the particles. This opens remarkable possibilities to replace materials like medical-grade steel by such composites.

The object is further achieved by an autoclavable medical instrument having a hollow space therein, said hollow space being filled with a composite containing a cured adhesive having distributed solid particles therein, wherein said solid particles being crowded together into a possible minimum of space.

In further embodiments autoclavable medical instruments result when using the different embodiments of the aforementioned methods.

It will be appreciated that the afore-mentioned and features and those still to be explained below can be used not only in the cited combination, but also in other combinations or singly, without leaving the scope of the present invention.

BRIEF DESCRIPTION OF THE DRAWINGS

The invention is described and explained in more detail below with reference to the attached drawing, in which.

DETAILED DESCRIPTION OF PREFERRED EMBODIMENTS

Figure 1:
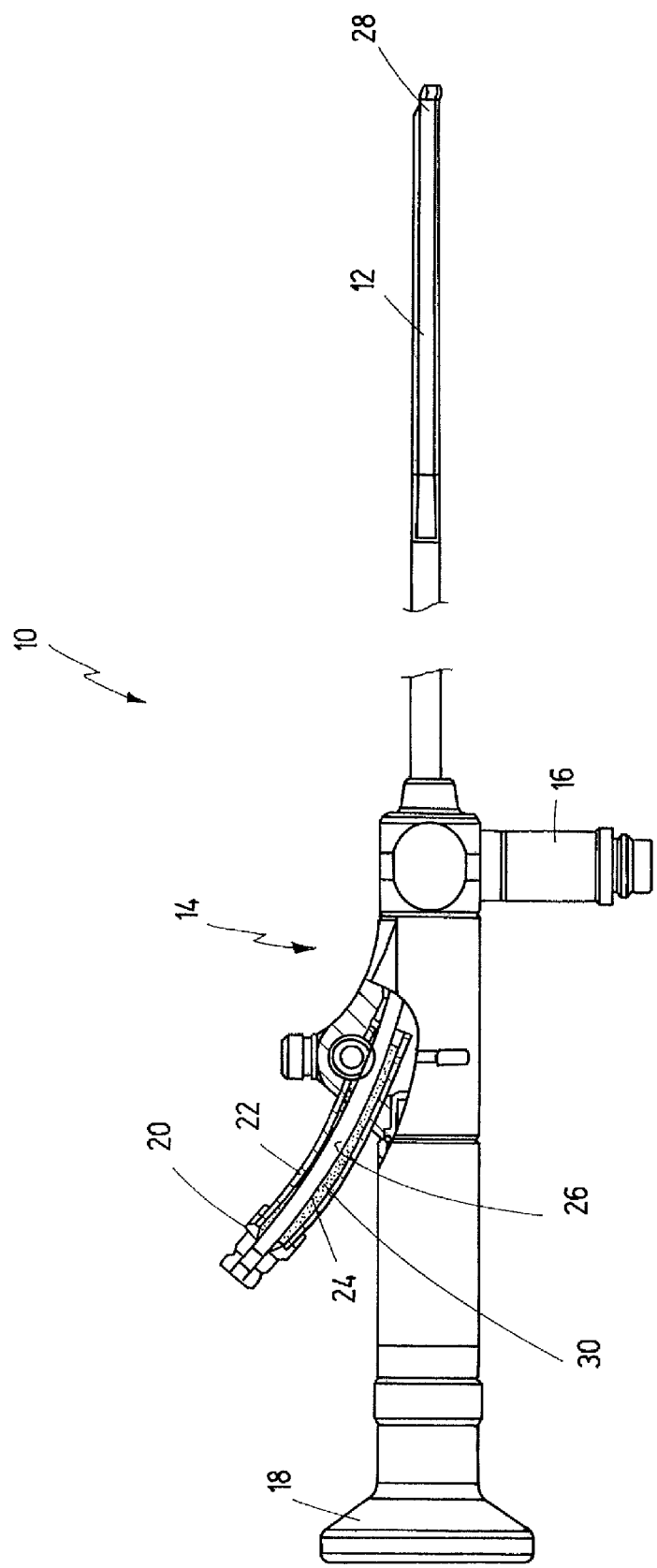
FIG. 1 shows a side view, partially in cross section of a medical instrument with an adhesive seal according to the invention.
Figure 2:
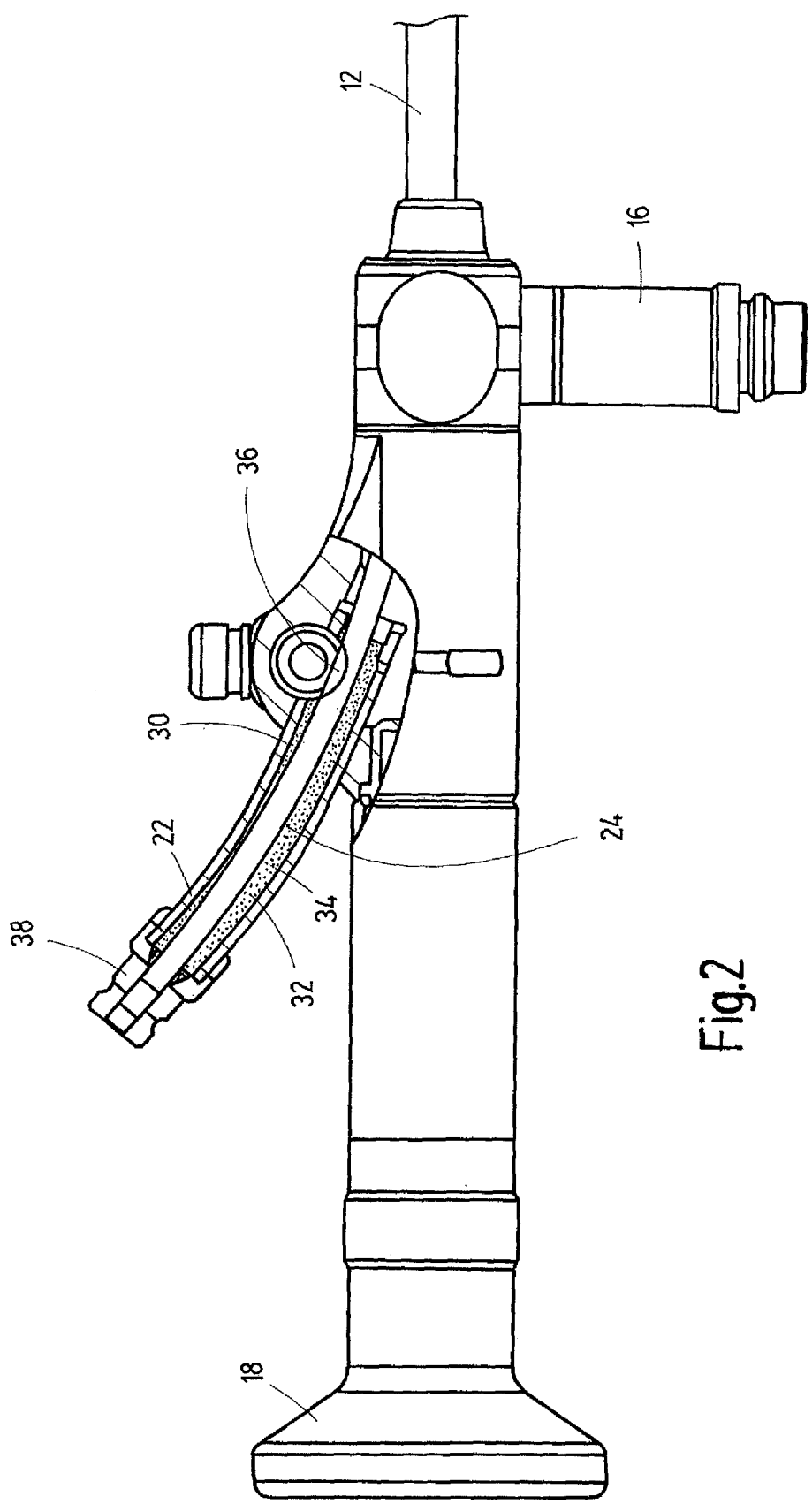
FIG. 2 shows an enlarged side view of the instrument of FIG. 1, and FIG. 3 a much or enlarged section of a medical instrument showing a hollow space which is filled according to the method of the present invention.

A medical instrument shown in FIGS. 1 and 2 is designed overall by reference number 10.

The medical instrument is a ureterorenoscope or a ureteroscope.

The instrument 10 has a shaft 12 whose proximal end is received in a housing 14.

A light-guide attachment 16 protrudes laterally from the housing 14. At its proximal end, the housing is provided with an eyepiece 18.

A lens system (not shown in any detail here) is received in the shaft 12 in order to permit observation through the shaft 12 from the eyepiece. The lateral light-guide attachment 16 is used to guide light to the distal end 28 of the shaft by way of a light guide likewise guided in the shaft. The shaft 12 is relatively thin, such that is can be inserted into a urethra, for example.

An attachment 20 protrudes laterally, in a curved shape, from the housing. A working instrument can be inserted into the shaft from the side via the curved attachment 20 and can be used to perform manoeuvres either in the ureter itself or in the bladder.

As will be seen from the cross-sectional detail, the curved attachment 20 comprises an outer reinforcing tube 22 in which an inner tube 24 is received. The inner tube 24 defines the working channel 26 through which the working instrument can be inserted into an inner working channel (not shown in any detail here) in the shaft 12. This means, that the inner tube 24 merges into a rectilinear portion that opens out at the distal end 28 of the shaft 12. It will be seen from the cross-sectional detail that the curves of the outer reinforcing tube 22 and the inner tube 24 are different. A hollow space 30 is therefore present between the outer face and the inner tube 24 and the inner face of the reinforcing tube 22, into which hollow space 30 an adhesive 32 is cast that contains a filler 34. This not only provides positional fixing but also has the effect that the space 30 between the inner tube 24 and reinforcing tube 22 is sealed off from the outside.

From the cross-sectional detail in FIG. 2, it will be seen that a transverse attachment 36 also opens into the working channel 26, for example in order to be able to deliver suction liquids or irrigation liquids through the working channel 26 alongside the working instrument. As will be seen in particular from the enlarged detail in FIG. 2, the transverse attachment 36 cuts through the sealing compound.

A filler 34, composed of spherical metal particles with a particle size in the range of 50 to 150 µm, is worked into the adhesive 32 at elevated temperatures (50-70° C.) a temperature at which the adhesive has a low viscosity which viscosity is similar to the viscosity of water. In the heated adhesive 20 to 80% by volume of the filler is introduced.

The particles can also be disc-shaped, ring-shaped, cube-shaped or generally polyhedral particles, for example flakes.

The instrument 10 can be assembled by mounting both the reinforcing tube 22 and also the inner tube 24 in the housing 14. An end cap 38 is not yet applied at this stage, such that the space 30 between the inner tube 24 and the reinforcing tube 22 is accessible from the outside. A heated mixture of adhesive 32 and filler 34 is introduced from the outside, for example through a syringe into the space 30. The instrument 10 has already been pre-heated in an oven to about 60° C., such that the compound made of adhesive 32 and filler 34 maintains the low viscosity state with the result that the space 30 can be filled completely, in particular in a manner free of air and bubbles. The escape of air from the space 30 can be further promoted by appropriately tapping or orienting the attachment 20 in the vertical orientation. It is also possible, for a brief period, to set the assembly in vibration using an ultrasonic appliance.

The instrument is held in that orientation for a couple of minutes to allow the particles to sink down due to gravity and to build up a package of minimum space.

The assembly is then introduced in a curing oven and heated to the curing temperature (about 135° C.).

After the adhesive has cured, the end face of the attachment is worked, for example ground, and the cap 38 is fitted.

The transverse attachment 36 can then be formed by drilling.

The union between cured adhesive compound and the metal tubes 22 and 24 is so intimate that this kind of working involving removal of material (i.e. drilling) can be carried out without causing cracks.

It is also possible to design the assembly of the curved attachment 20 as a structural part that can be detached from the housing 14 and to form the adhesive seal away from the instrument 10 and then to mount this assembly on the housing.

Since, as has already been mentioned, the adhesive 32 with the filler 34 provides an adhesive seal which withstands strong conditions during cleaning and in particular during autoclaving of such instrument, the working channel 26 can also be formed in another way. Such strong condition can also occur, for example, if a medical instrument inaccidently falls down from a table. Instead of the inner tube 24, a suitable configured wire, for example, a suitable cord could be inserted which is removed again after the adhesive has cured. It is possible to coat the wire or cord with a releasing or a compound for preventing adhesion. This means, the working channel 26 is directly formed within the cured mass of the adhesive 32 without providing an inner tube 24. In that case, the cured adhesive surrounds the working channel 26. This will be used in case of a specially curved or twisted-working channels, which cannot produced by machining. This, by virtue of the fact, that according to this invention the filler results in an adhesive seal that can withstand strong conditions to where the medical instruments are exposed during handling and during the subsequent cleaning and autoclaving.

Figure 3:
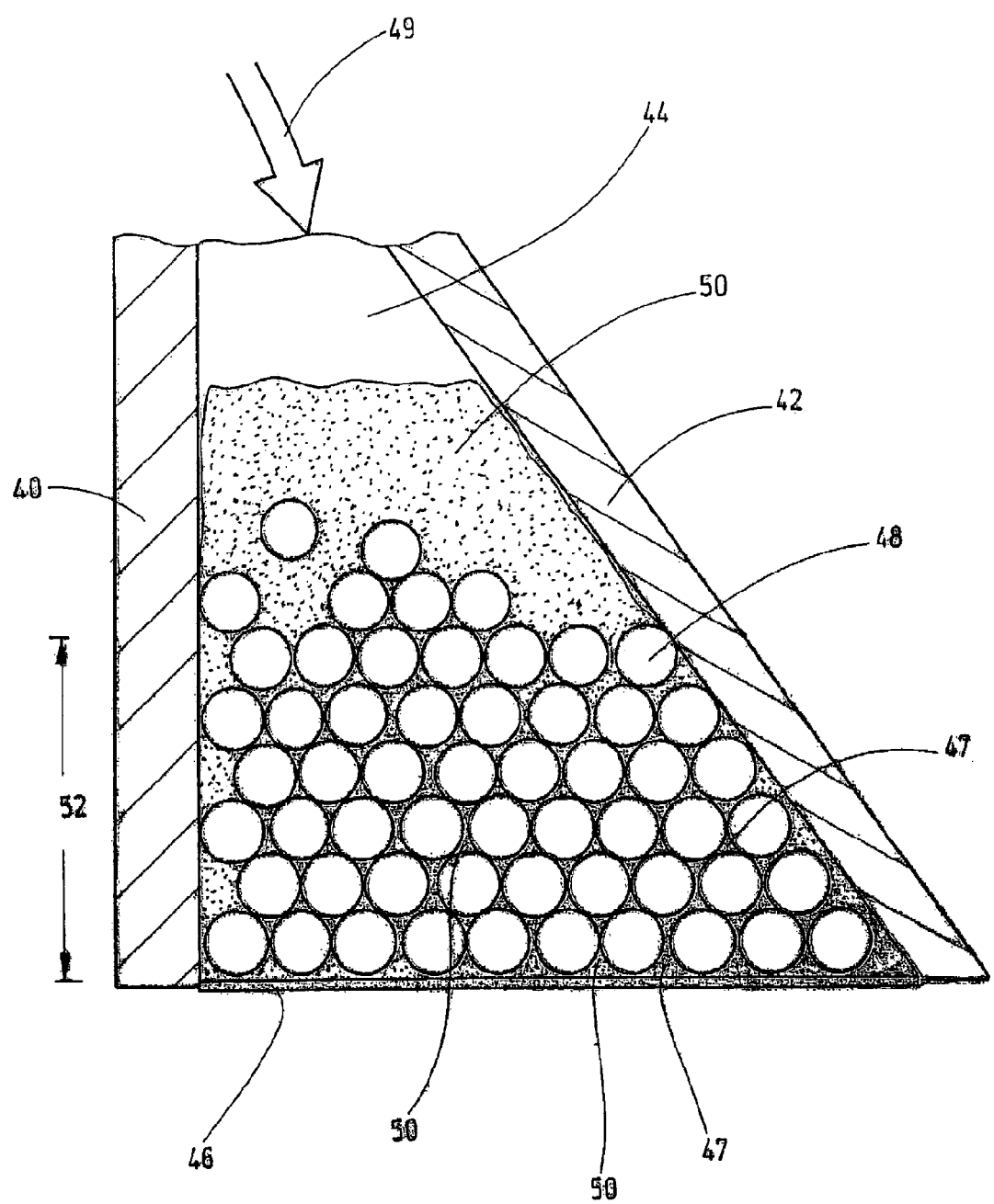

FIG. 3 shows a hollow space 44 between two parts 40 and 42 which are mold with the method according to the invention.

The hollow space 44 between the parts 40 and 42 is first closed by a closure 46, if this side faces to the outside.

The heated adhesive of low viscosity having mixed in particles 48 in the shape of balls is poured from "upside" into the hollow space 44 as indicated by an arrow 49. The balls are made of a metallic powder whose density is higher than the density of the low viscosity adhesive. The viscosity of the adhesive is in the viscosity of water. The particles 48 now have a certain period of time to sink downwardly following the gravity and pack or crowd to a close ball package.

This packaging can, as mentioned above, supported by vibrating the parts.

Ideally, the particles 48 pack to a most closest ball package. In the free spaces 47 between the particles 48 and between the particles 48 and the parts 40 and 42 the still water-liquid adhesive is distributed uniformly.

FIG. 3 shows a situation in which only a lower area 52 of the hollow space 44 is occupied with the closest ball packaging. The area 52 is, after a certain transitional stage of more or less regularly distributed balls, followed by an area, which is filled with hardened adhesive 50 only.

This design within the hollow space 44 can be used, if the two parts 40 and 42 have to be sealed only via the outside, which is in the presentation of FIG. 3 the bottom side. It is excluded, that within the area 52 brittles or cracks can cure, which can allow the penetration of gases or liquids from the outside, this also after numerous autoclaving processes.

If brittles occur in areas where the cured adhesive 50 is predominated that is not critical.

But, if it is desired to fill the hollow space 44 entirely with particles, it is possible to fill the inner space more and more with the mixture of liquid adhesive allowing the particles to sink down and to pour more and more liquid adhesive/filler mixture into the space. A surplus of pure liquid adhesive is removed.

When starting the method, the volume percentage of the particles in the adhesive of low viscosity can be relatively small, for enhancing the pouring or penetrating of the liquid adhesive/particle mixture into the very small or possible narrow hollow space 44. After sinking down of the particles due to gravity the area 52 with the compact closest ball packaging is build up step by step.

If desired to fill the entire hollow space one can use a higher percentage of particles in the liquid adhesive/particle mixture but, this does not enhance the handling. Therefore, one fills in as long as the entire hollow space 44 is packed with the particles.

After having the desired package condition the adhesive is cured.

As mentioned above, it is also possible to work with particles which are swimming on the liquid adhesive.

Under this conditions one has to pose the structure shown in FIG. 3 upside down and to fill it with the liquid adhesive/particle mixture from the bottom side in that more and more particles will swim on the upper side and pack to a compact closest ball packaging.

The final closure 56 can be removed after the composite material is cured or it can be poured into the composite if desired.

What is claimed is:

1. An autoclavable medical endoscopic instrument, having a hollow space therein, said hollow space being filled with a composite containing a cured adhesive having distributed solid metal particles therein, wherein, at least in an area of said hollow space, said solid metal particles being packed together into a most dense particle concentration, which is possible due to its geometry, without changes of an original size and geometry of said solid metal particles, wherein said cured adhesive fills free spaces between said packed solid metal particles and wherein a material of said solid metal particles is chosen such that said material has a thermal expansion property substantially similar to a thermal expansion property of structural metal elements defining said hollow space.

2. The autoclavable medical endoscopic instrument of claim 1, wherein said packed solid metal particles are contained in amount of 50-80% per volume.

3. The autoclavable medical endoscopic instrument of claim 1, wherein said solid metal particles have a size in a range of 50 µm to 150 µm.

4. The autoclavable medical endoscopic instrument of claim 1, wherein the geometry of said solid metal particles is selected from the group of spherical particles, disc-like particles, ring-like particles, cubic or polyhedral particles.

5. The autoclavable medical endoscopic instrument of claim 1, wherein said solid metal particles are made of an electric-conducting material.

6. The autoclavable medical endoscopic instrument of claim 1, wherein said solid metal particles are made of a heat-conducting material.

7. The autoclavable medical endoscopic instrument of claim 1, wherein said metal is magnetic.

8. The autoclavable medical endoscopic instrument of claim 1, wherein there is a transitional stage of more or less packed particles between an area of closest packing to an area of predominantly containing adhesive.

\* \* \* \* \*